United States Patent [19]

Cooper

[11] Patent Number: 4,672,955

[45] Date of Patent: Jun. 16, 1987

[54] ORTHOSIS, METHOD OF MAKING AND KIT THEREFOR

[75] Inventor: Adriaan Cooper, Huntington, Conn.

[73] Assignee: United Technologies Corporation, Hartford, Conn.

[21] Appl. No.: 869,522

[22] Filed: Jun. 2, 1986

[51] Int. Cl.$^4$ ............................................. A61F 3/00
[52] U.S. Cl. ............................... 128/80 F; 128/89 R; 156/275.5
[58] Field of Search ................. 128/80 R, 80 C, 80 F, 128/82, 89 R, 90; 264/222, 223; 156/182, 275.5

[56] References Cited

U.S. PATENT DOCUMENTS

| | | | |
|---|---|---|---|
| 4,553,535 | 11/1985 | Finnieston et al. | 128/88 |
| 4,565,190 | 1/1986 | Pirmantgen et al. | 128/80 |
| 4,572,167 | 2/1986 | Brunswick | 128/78 |
| 4,572,169 | 2/1986 | Mauldin et al. | 128/80 |

FOREIGN PATENT DOCUMENTS 870150  5/1971  Canada ................................. 128/90

OTHER PUBLICATIONS

"Warm'n Form", Thermo Mold Medical Products, Inc.—brochure, 6 pages, 1974.
Dobi-Symplex, Inc., Winter Park, Fla. (Catalogue--complete).
"PSSI Ankle Stabilizer", Physical Support Systems, Inc., 1 page.
"Scott-Craig TM Paraplegic Orthoses", Scott Orthotic Labs, 4 pages.
"The Genucentric Knee Orthosis-A New Concept", R. Foster, J. Milani, Orthotics and Prosthetics, vol. 33, No. 2, pp. 31-44, Jun. 1979.
"Carbon Fibre Reinforced Plastic Applied to Prosthetics and Orthotics", Nelham, J. Biomed. Engng. 1981, vol. 3, Oct., pp. 305-314.
"The Only Self Molding Immediate Fit Orthotic", Dr. A. Blomer, 14 pages.
"Mold-A-Brace", C. H. Martin Company, 4 pages.
"Spiral Ankle-Foot Orthosis (AFO)", RTC, 2 pages.
"Knee-Ankle-Foot Orthosis", United States Manufacturing Company, 1 page.
"The ACL Dilemma", Townsend Industries, Inc., 13 pages.

Primary Examiner—Clifford D. Crowder
Attorney, Agent, or Firm—Gerald E. Linden; Andrew N. Parfomak

[57] ABSTRACT

The thigh and calf bands of a knee orthosis are formed of a layer (or layers or curable composite material. The sidebars are integral with the thigh and calf bands in that they are simply extensions of the layers forming the thigh and calf bands. The sidebars are cured prior to fitting the thigh and calf bands about the leg, but the thigh and calf bands are left incured so that they may be formable about the leg and cured in place thereon.

A method for fabricating the orthosis is disclosed and a kit therefor is described.

The invention is also suitable for an ankle orthosis.

7 Claims, 8 Drawing Figures

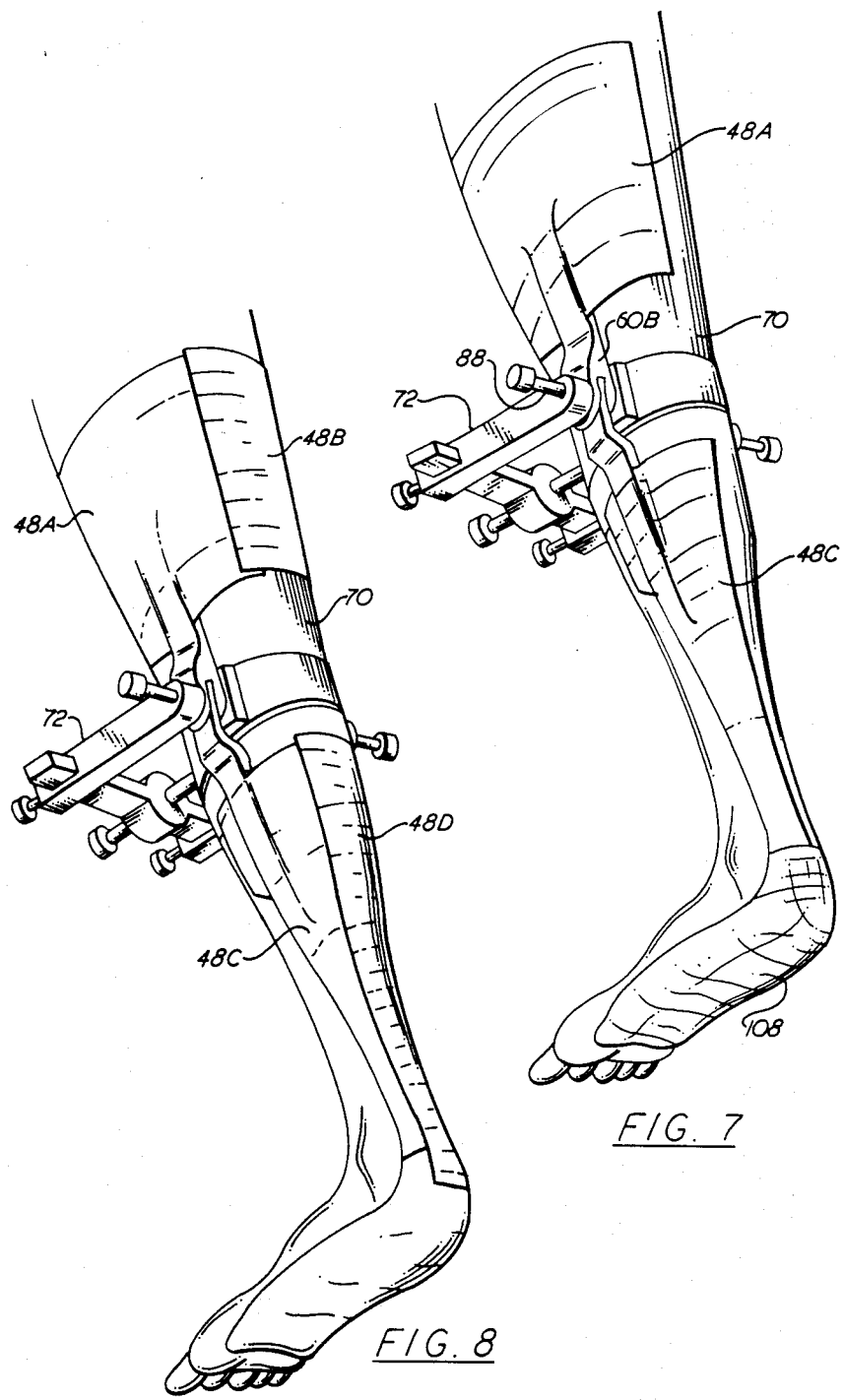

ORTHOSIS, METHOD OF MAKING AND KIT THEREFOR

TECHNICAL FIELD OF THE INVENTION

The invention relates to orthoses and, more particularly, to a knee, ankle, or knee-ankle-foot orthosis.

BACKGROUND OF THE INVENTION

A knee orthosis (KAFO) is a leg brace having an upper section removably attached about the upper leg and a lower section removably attached about the lower leg. The two sections are hinged together by sidebars on the medial (inner) and lateral (outer) side of the leg to allow for knee movement. It is termed a knee-ankle-foot orthosis (KAFO) when the lower orthosis section extends down around the ankle and underneath the foot to provide greater attachment stability and to transmit forces from the foot to the upper leg.

Conventional KAFO's are assembled in the following manner. During the first session with the patient, measurements are taken and a female cast is made of the leg. From the female cast a male cast is made, which is a replica of the leg. Measurements are transferred onto the male cast. Thigh and calf bands and sidebars are made to fit the male cast. This includes bending the rigid metal sidebars into S-shapes to conform with the contours of the leg. The various components are then riveted together to complete the KAFO. During the second session with the patient, the KAFO is fitted to the patient's leg. Modifications may be necessary to achieve a proper fit.

This method is labor intensive and inconvenient as it requires at least two sessions with the patient. Furthermore, the conventional KAFO, being made up of metal, plastic and sometimes leather, is not aesthetically pleasing, and tends to become noisy after it has been in use for some time.

DISCLOSURE OF THE INVENTION

It is an object of this invention to provide a KAFO that is lighter, more comfortable, more aesthetically pleasing, quieter, and easier to fabricate and fit than conventional KAFO's.

According to the invention, the thigh and calf bands of a knee orthosis are formed of several layers of UV-curable composite material. The sidebars are integral with the thigh and calf bands in that they are simply extensions of the layers forming the thigh and calf bands. The sidebars are cured prior to fitting the thigh and calf bands about the leg, but the thigh and calf bands are left uncured so that they may be formable about the leg and cured in place thereon.

A method for fabricating the orthosis is disclosed and a kit therefor is described.

The invention is also suitable for an ankle orthosis.

Other objects, features, and advantages of the invention will become apparent in light of the following description thereof.

BRIEF DESCRIPTION OF THE DRAWINGS

FIG. 7 is a perspective view of the subassemblies of FIG. 4 fitted over a patient's leg (medial);

FIG. 8 is a perspective view of the subassemblies of FIG. 4 fitted over a patient's leg (lateral).

Figure 6:
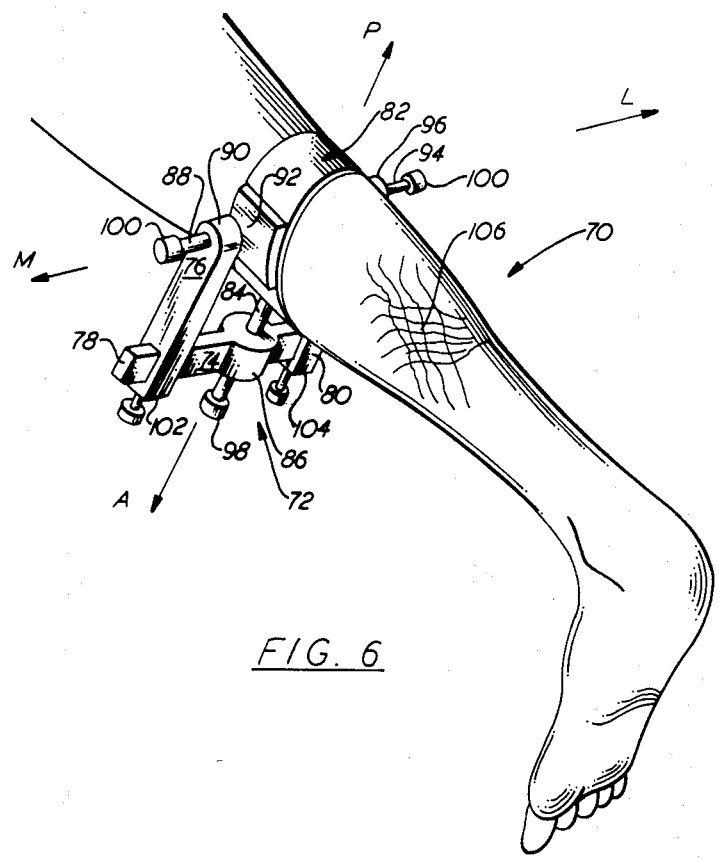
FIG. 6 is a perspective view of a joint fixture used in conjunction with fitting the KAFO of this invention to a patient's leg.

The following orientations, used throughout this description are noted in FIG. 6; anterior (A), posterior (P), medial (M), and lateral (L). Further, the following terms, distal and proximal are used to indicate orientation toward and away from the knee joint, respectively.

BEST MODE FOR CARRYING OUT THE INVENTION

Figures 1, 2:
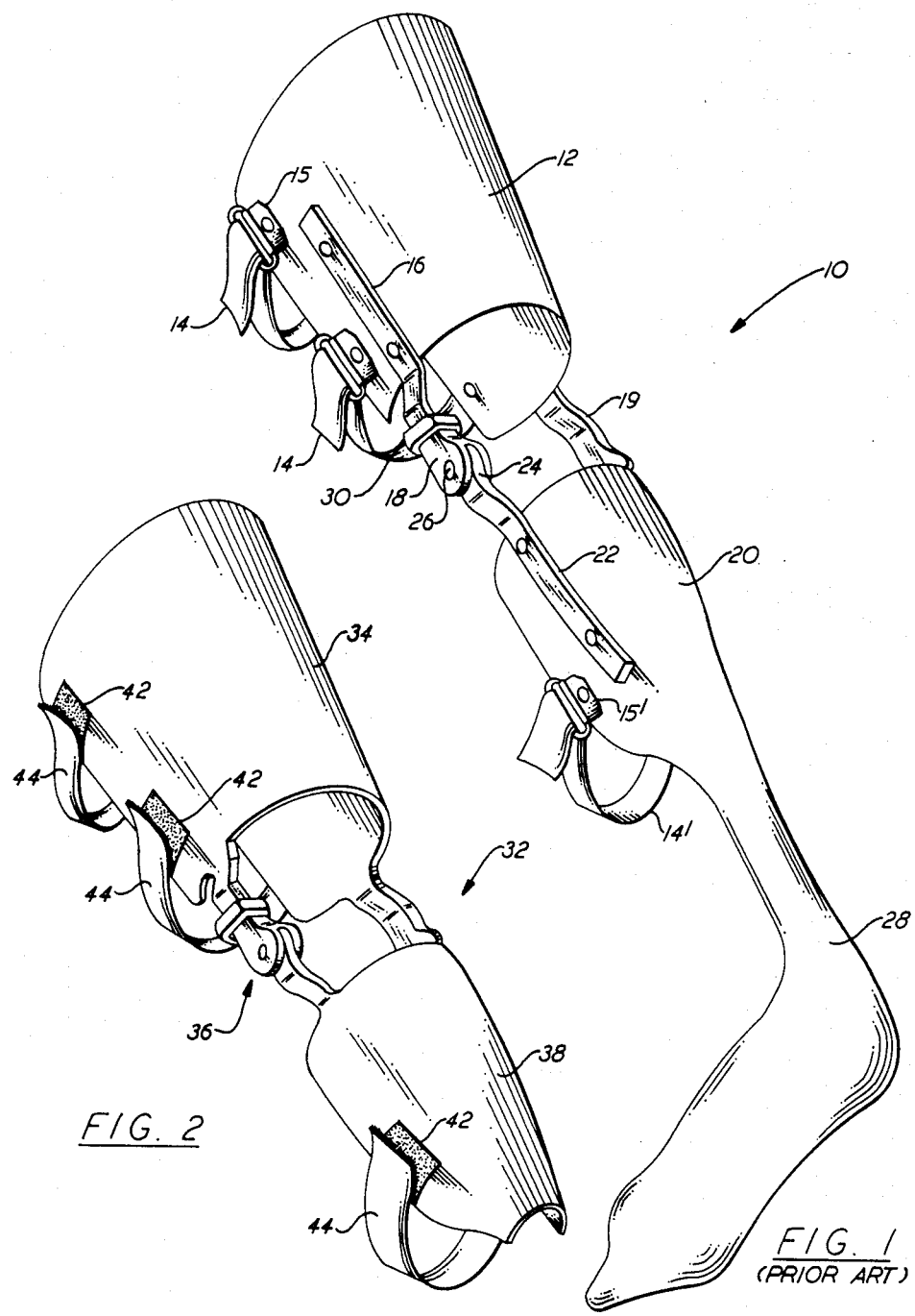
FIG. 1 is a perspective view of a prior art KAFO.
FIG. 2 is a perspective view of the orthosis of this invention, in finished form.

FIG. 1 shows a prior art KAFO 10. A rigid thigh band 12 partially encircles (approximately 250°) of the thigh, from the medial side around the posterior side and to the lateral side of the leg (leg not shown). Straps 14 and associated hardware 15 are riveted to the thigh band 12 to secure the thigh band to the patient's upper leg. A rigid metallic side bar 16 is riveted to the medial side of the thigh band 12 and extends longitudinally downward beneath the thigh band to the area of the patient's knee (not shown), where it terminates in a clevis 18. A similar sidebar 19 is riveted to the lateral side of the thigh band 12.

Similarly, a calf band 20 encircles approximately 250° of the calf, from the medial side around the posterior side to the lateral side of the leg. A strap 14' and associated hardware 15' are riveted to the calf band 12 to secure the calf band to the patient's calf. A rigid metallic sidebar 22 is riveted to the medial side of the calf band 20 and extends longitudinally upward above the calf band to the area of the patient's knee, where it terminates in a lug 24 that is pivotally attached by a pin 26 to the clevis 24. A similar sidebar (not visible) is riveted to the lateral side of the calf band. The calf band 20 includes a rigid ankle and foot orthosis 28, as illustrated.

A drop lock ring 30 is slideable over the thigh sidebar 16 and 19 to immobilize the hinged joint formed by the lug 24 and clevis 18 of the medial sidebars 16 and 22. A similar drop lock ring (not shown) is similarly provided for the lateral sidebars.

FIG. 2 shows the knee orthosis 32 of this invention, which is made from suitable preimpregnated composite materials such as glass fiber fabric impregnated with polyester resin that can be cured by UV radiation from a suitable light source. One such material is PALATAL ® KR55-54I (available from BASF). The KAFO 32 comprises a thigh band 34 connected by medial and lateral hinges 36 to a calf band 38. Instead of being an assembly of many discrete components like the KAFO 10 of FIG. 1, the knee orthosis 32 is formed of only a few integral structures. It consists of four prefabricated, partly cured subassemblies (i.e., parts of which are cured and parts of which are uncured) that are fitted to the patient's leg in-situ, and fully cured (i.e. the uncured parts are cured) on the patient's leg. Hook pads 42 and loop straps 44 (corresponding to the straps 14,14' and hardware 15,15' of FIG. 1), such as VELCRO ® straps, are glued to the thigh band 34 and to the calf band 38 (corresponding to the thigh band 12 and to the calf band 20 of FIG. 1) to complete the knee orthosis. The subassemblies are prefabricated and partly cured to provide rigidity in the hinge areas 36 while not affecting their ultimate formability on the patient's leg. The knee orthosis 32 is prefabricated and fitted to the patient in the following manner.

Figure 3:
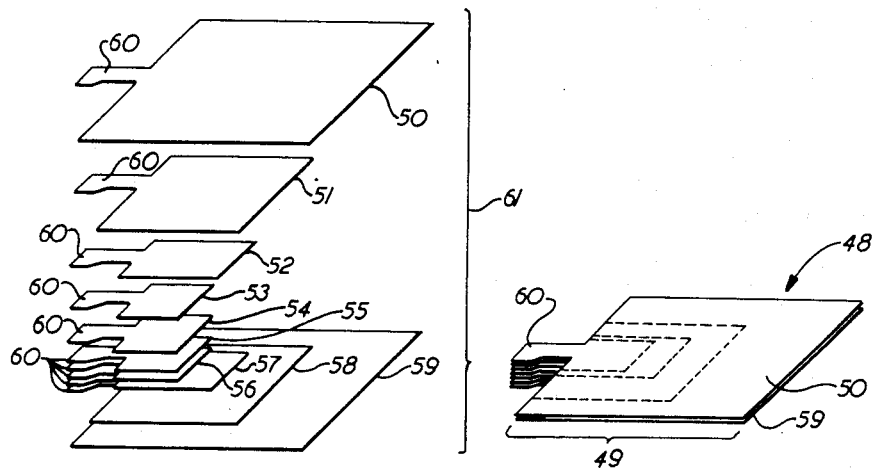
FIG. 3 is a schematic of the subassemblies used to create the orthosis of this invention.

FIG. 3 shows the prefabrication of a typical subassembly 48. Two such subassemblies 48A and 48C are required to form one side (e.g., the medial side) of the thigh band 34 and calf band 38, respectively. A second set of subassemblies 48B and 48D is required to form the other side (e.g., the lateral side) of the thigh band 34 and calf band 38, respectively. The subassemblies 48A and 48B form the thigh band 34, and the subassemblies 48C and 48D form the calf band 38.

Each subassembly is fabricated of a plurality of layers of material, each layer having a generally rectangular base portion 49 and an elongated sidebar portion 60 extending integrally from the proximal edge of the base portion. By "integrally" it is meant that the sidebar portion 60 is formed from at least some of the same layers of material that form the base portion. The individual layers are assembled as indicated by the bracket 61 so that the proximal edges of the base portions are in register, and the sidebar portions 60 of each layer are in register. Preferably, the base portions are of successively smaller dimension from the two outermost layers 50,59 to the centermost layer 54,55. This manner of fabrication provides for a subassembly with favorable load distributing characteristics.

In the context of the knee orthosis 32 of this invention, "sidebar" means the integrally extending sidebar portion of each subassembly, and should not be confused with the discrete members ("sidebars") which are attached to the thigh and calf bands common in the prior art.

The base portions 49 are masked and the subassemblies 48 are exposed to ultraviolet light for about 10 minutes depending on the UV light source and the UV resin used, so that the sidebar portions 60 are cured while the base portions 50–59 remain uncured and hand formable. The uncured resin in the base portion 50–59 has sufficient "tackiness" to hold the layers together.

The four subassemblies used (as depicted on FIG. 8) for each knee orthosis 32 are:

a medial thigh band subassembly 48A extending from the posterior side around the medial side of the patient's thigh;

a lateral thigh band subassembly 48B extending from the posterior side around the lateral side of the patient's thigh;

a medial calf band subassembly 48C extending from the posterior side around the medial side of the patient's calf; and a lateral calf band subassembly 48D extending from the posterior side around the lateral side of the patient's calf.

The sidebar portions 60 of the subassemblies are trimmed after curing to form a lug 60A (corresponding to the lug 24 of FIG. 1), or a clevis 60B (corresponding to the clevis 18 of FIG. 1). For prefabricating a clevis, the two innermost layers 54 and 55 of the sidebar portion 60 are separated (spaced-apart) prior to the aforementioned curing thereof, either by a removeable mandrel, by inserting a suitable wedgelike plug made of prepreg plies, or a translucent material such as PLEXIGLAS ®.

Figure 4:
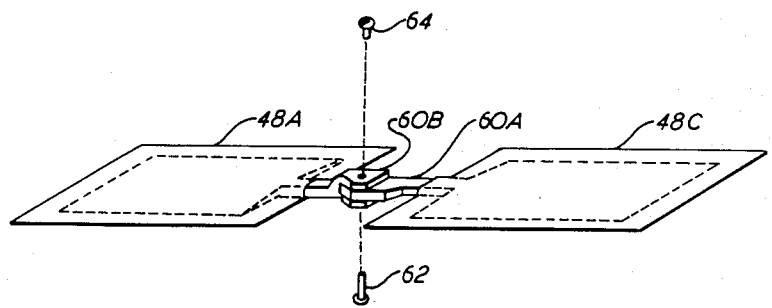
FIG. 4 is a schematic of two subassemblies of FIG. 3 being assembled together.

FIG. 4 shows the medial thigh band subassembly 48A having a clevis sidebar portion 60B, and the medial calf band subassembly 48C having a lug sidebar portion 60A. Appropriate holes are drilled in the sidebar portions 60A and 60B, and a bushing 62 is secured therein by a bolt 64, or other suitable fastening means. A drop lock ring is optional, and may be fabricated as shown in FIG. 5.

Figure 5:
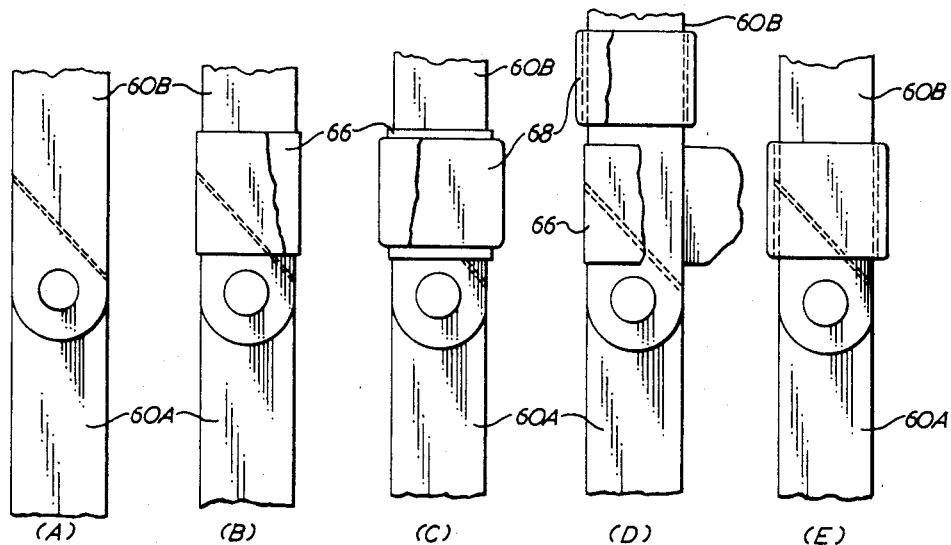
FIG. 5 is a schematic of a detail relating to the two assembled subassemblies of FIG. 4.

FIG. 5 shows the steps A–E for fabricating a drop lock ring in-situ. In a first step A, the clevis 60B and the lug 60A are aligned in the stretched-out, or in-line, position. In the next step B, the clevis is wrapped with Teflon ® tape 66 in an area that overlaps the lug. Next, in the step C, preimpregnated composite tape 68 of suitable material and dimension is wrapped about the Teflon ® tape 66 a sufficient number of turns to provide the required drop lock ring thickness. The composite tape 68 is then fully cured, either by UV light (in the case of UV curable resin) or at room temperature by choosing a material for the composite tape 68 that is impregnated with room temperature curing resin. Next, in the step D the fully cured tape 68, which forms the cured drop lock ring, is slid off of the Teflon ® tape 66, and the TEFLON ® tape is removed. The drop lock ring 68 is now ready to be slid into position over the clevis/lug joint when desired, as shown in the step E.

With or without the drop lock ring, as desired, the lug and clevis of the medial thigh and calf subassemblies 48A,48C, and similarly the lug and clevis of the lateral thigh and calf subassemblies 48B,48D are assembled with bushings 62, and are placed in a kit.

FIGS. 6–8 show how the KAFO 40 is assembled and fitted to a patient's leg.

FIG. 6 shows a patient's leg 70 fitted with a joint fixture 72 in preparation for fitting the knee orthosis 32 of this invention. The joint fixture 72 is essentially a U-shaped bracket having the following elements:

a first elongate member 74 disposed transversely (medial-to-lateral) anterior to the knee;

a second elongate member 76 extending posteriorly past the patient's knee from the medial end 78 of the first elongate member 74;

a third elongate member 80 extending posteriorly past the patient's knee, from the lateral end of the first elongate member 74;

a locator strap 82 removably fixed about the patient's knee, such as by VELCRO fasteners (not shown);

an attachment pin 84 extending from the midsection 86 of the first elongate member 74 to the locator strap 82, and suitably affixed thereto at the anterior of the knee;

a medial hinge centering pin 88 extending from the posterior end 90 of the second elongate member 76 to the locator strap 82 at the medial side of the knee joint, and urging thereagainst via a pad 92; and a lateral hinge centering pin 94, coaxial to the medial hinge centering pin 88, and extending from the posterior end 96 of the third elongate member 80 to the locator strap 82 at the lateral side of the knee joint, and urging thereagainst via a pad (not visible).

The anterior/posterior location of the joint fixture 72 relative to the knee is adjusted in the following manner. The attachment pin 84 is threaded through the midsection 86 of the first elongate member 74 so that by turning a knob 98 on the anterior end of the attachment pin, the entire joint fixture 72 may be positioned closer to/farther away from the knee. This is significant in the context of properly locating the hinge centering pins 88 and 94 coaxial to the axis of the knee joint itself. (A pin 84 slideable through the midsection 86 of the first elongate member and an appropriate set screw securing the pin 84 would also allow for this adjustment).

The hinge centering pins 88 and 94 may be spring loaded in their respective elongate members 76,80 to urge against the locator strap, or may be threaded through the respective posterior ends 90,96 thereof and urged against the pads 92 by turning knobs 100 located on their respective medial and lateral ends. In either case, the anterior ends 102, 104 of the second and third elongate members 76,80 may be slideably attached to the medial and lateral ends of the first elongate member 74 (as illustrated) so that they may be coarsely fixed in a range of positions to accommodate various patients.

A protective sock 106 is placed over the leg 70 prior to fitting the joint fixture 72 to the patient.

FIG. 7 shows the thigh and calf band subassemblies 48A,48C fitted in place on the patient's leg and located by the joint fixture. The medial hinge centering pin 88 extends through the holes in the clevis 60B and the lug 60A with the bushing. The base portions of the medial thigh and calf band subassemblies are formed around the patient's leg, by hand, and then may be partially-cured by exposure to UV light, such as for one-half of the required full cure time (to retain their shape while allowing some formability without severely impairing bondability). Some trimming, such as by scissors, of these subassemblies is appropriate at this time, but the posterior edges of the base portions of the subassemblies should extend slightly beyond the extreme posterior longitude of the leg for overlapping by the lateral subassemblies, as described hereinafter. In the area of overlap, the subassemblies stick together due to the tackiness of the resin, which also tacks the subassemblies to the sock 106.

At least one of the calf band subasemblies 48C, 48D may extend sufficiently distally to embrace the ankle and receive a foot assembly.

Finally, as shown in FIG. 8, the lateral thigh and calf band subassemblies 48B,48D are located by the joint and formed about the patient's leg. Note the overlapping posterior edges of the base portions of the respective medial/lateral thigh and calf band subassemblies. The entire assembly is then fully cured by exposure to UV light, removed from the patient's leg, finally trimmed, the screws 64 inserted into the bushings 62, and looks like the knee orthosis of FIG. 2 in FIG. 8 (but now it is a KAFO).

In order to prevent chafing between the straps 44 and the patient's leg (and likewise from the sharp anterior edges of the thigh and calf bands) it is possible to size (dimension) at least a few of the plies (e.g., 50,51) of the base portions so that their anterior edges overlap on the anterior surface of the leg. Of course, in the curing process the subassemblies must be prevented from sticking to one another in this region, which is readily achieved by inserting a release ply (film) between the overlapping edges during the curing process. When fully cured, these few layers forming the anterior anti-chafing flap will remain sufficiently flexible for attaching/removing the orthosis from the leg.

As is known, knee joints other than the single axis knee joint disclosed are suitable to a knee orthosis. Some alternatives are the Polycentric Joint and the Genucentric Joint. Alternative joints are readily incorporated into the orthosis of this invention.

It should be understood that certain changes could be made to the sequence described. Additionally, if the KAFO has to effect substantial corrections in leg support and/or gait, it may be necessary to make a cast replica of the leg and modify the KAFO. The integral composite KAFO will then be laid up on the modified cast replica instead of on the patient's leg.

The preferred composite material is a glass fiber fabric/polyester system that can be cured with ultraviolet light, but another suitable material may be used. What is meant by "suitable composite material" is any composite which is curable by exposure to ultraviolet light. Further, not all layers in the subassembly need be UV-curable composite material but may include any material with acceptable strength and formability characteristics.

Selective reinforcement with graphite unidirectional tape or fabric is possible to a limited extent. (Obviously, an opaque fabric would impair the penetration of ultraviolet light into the layers.) If much higher stiffness is required than is attainable with glass fabric, a low temperature curable graphite prepreg could be used. The KAFO will then have to be assembled on a cast replica of the leg.

It should also be understood that other joints, such as the ankle joint may have an orthosis fabricated in an accordingly similar manner to that of the knee orthosis described herein. In that context, "ankle" would be substituted for "thigh", "ankle joint" for "knee" and "foot" for "calf".

The advantages of this invention are:

labor content is reduced by approximately 50% compared with old method.

Less effort is needed to achieve proper fit.

If extensive corrections in leg support and/or gait are required, the KAFO would have to be assembled on a modified cast replica of the leg (see alternate methods of construction). Labor content reduction would be approximately 10%.

The integral composite KAFO will be approximately 15% lighter than a comparable current KAFO using steel sidebars.

The integral composite KAFO has thinner shell walls than a comparable current KAFO. This, combined with the weight reduction, increases comfort.

The integral composite KAFO is aesthetically more pleasing than a current KAFO.

The integral composite KAFO is expected to generate less noise than a current KAFO.

It should be understood that heat curable composite material could be employed rather than the UV-curable composite materials described herein. For instance a blocked polymer which is activated (for curing) at a temperature slightly higher than room temperature, and curing with a heat lamp or hair dryer is contemplated.

I claim:

1. A knee orthosis fittable about a calf and thigh comprising:
 four subassemblies of a composite material each subassembly containing at least one layer curable by exposure to ultraviolet radiation;
 a first of the four subasssemblies formably fittable about the medial and posterior sides of the thigh, and having an integrally formed sidebar suitable to extend along the medial side of the knee;
 a second of the four subassemblies formably fittable about the lateral and posterior sides of the thigh, having an integrally formed sidebar suitable to extend along the lateral side of the knee, and overlapping at its posterior edge the posterior edge of the first of the four subassemblies;

a third of the four subassemblies formably fittable about the medial and posterior sides of the calf, and having an integrally formed sidebar suitable to extend along the medial side of the knee;

a fourth of the four subassemblies formably fittable about the lateral and posterior sides of the calf, having an integrally formed sidebar suitable to extend along the lateral side of the knee, and overlapping at its posterior edge the posterior edge of said third of the four subassemblies;

wherein the first and second of the four subassemblies are bonded to one another at the site of their overlapping posterior edges; and wherein the third and fourth of the four subassemblies are bonded to one another at the site of their overlapping posterior edges.

2. A knee orthosis as in claim 1 wherein the first and second of the four subassemblies are suitably sized to have overlapping anterior edges when in place on the leg, and the third and fourth of the four subassemblies are suitably sized to have overlapping anterior edges when in place on the leg, wherein the overlapping anterior edges of the first and second of the four subassemblies and of the third and fourth of the four subassemblies are not bonded to one another.

3. A knee orthosis as in claim 1 wherein the third and fourth of the four subassemblies extend sufficiently distally to formably fit about the ankle and further comprising an assembly formably fittable to the foot and bonded to the distal edges of the third and fourth of the four subassemblies.

4. A knee orthosis as in claim 1 wherein each of the subassemblies is constructed of a plurality of layers of composite material, each of the plurality of layers having a generally rectangular base portion, and each of the plurality of layers having an elongated sidebar portion extending integrally from one edge of the base portion;

wherein the sidebar portions of the plurality of layers of each subassembly are in register with one another;

wherein the proximal edges of the base portions of the plurality of layers of each subassembly are in register with one another; and wherein the base portions of the plurality of layers of each subassembly progressively decreases in area, from the outermost layers to the centermost layers.

5. A method of fabricating and fitting to a leg a knee orthosis comprising:

laying up several layers of UV-curable composite material to form each of four subassemblies, wherein each subassembly has a generally rectangular base portion and an elongated sidebar portion extending integrally from one edge thereof;

curing the sidebar portions;

fitting a first of the four subassemblies about the medial side of the thigh;

fitting a second of the four subassemblies about the lateral side of the thigh so that the posterior edge of the base portion of the second of the four subassemblies overlaps the posterior edge of the base portion of the first of the four subassemblies on the posterior side of the thigh;

fitting a third of the four subassemblies about the medial side of the calf;

fitting a fourth of the four subassemblies about the lateral side of the calf so that the posterior edge of the base portion of the fourth of the four subassemblies overlaps the posterior edge of the base portion of the third of the four subassemblies on the posterior side of the calf;

curing in place on the leg the overlapping base portions of the subassemblies.

6. A method of fabricating and fitting to a leg a knee orthosis according to claim 5 wherein the anterior edges of the base portions of the first and second of the four subassemblies overlap on the anterior side of the thigh and wherein the anterior edges of the base portions of the third and fourth of the four subassemblies overlap on the anterior side of the calf, further comprising:

inserting a layer of release material between the overlapping anterior edges of the base portions of the subassemblies prior to curing in place on the leg the base portions of the subassemblies.

7. A knee orthosis kit having component subassemblies capable of being fitted to a leg comprising four subassemblies;

each subassembly containing at least one layer of curable composite material;

each subassembly having a base portion which is generally rectangular and which is uncured;

each subassembly having an integrally formed sidebar portion extending from an edge of the base portion and which is cured;

wherein;

a first subassembly is adapted to extend from the posterior side around the medial side of the thigh;

a second subassembly is adapted to extend from the posterior side of the thigh around the lateral side of the thigh and have its posterior edge overlap the posterior edge of the first subassembly;

a third subassembly is adapted to extend from the posterior side around the medial side of the calf;

a fourth subassembly is adapted to extend from the posterior side of the calf around the lateral side of the calf and have its posterior edge overlap the posterior edge of the third subassembly.

* * * * *